US00RE36991E

United States Patent [19]

Yamamoto et al.

[11] E Patent Number: Re. 36,991

[45] Reissued Date of Patent: Dec. 19, 2000

[54] BIOSENSOR AND METHOD FOR PRODUCING THE SAME

[75] Inventors: Tomohiro Yamamoto, Neyagawa; Mariko Miyashita, Nishinomiya; Toshihiko Yoshioka, Hirakata; Satoko Tsuji (nee Fujisawa), Katano; Shiro Nankai, Hirakata, all of Japan

[73] Assignee: Matsushita Electric Industrial Co., Ltd., Osaka-fu, Japan

[21] Appl. No.: 09/375,705

[22] Filed: Aug. 13, 1999

Related U.S. Patent Documents

Reissue of:

[64] Patent No.: 5,658,443
Issued: Aug. 19, 1997
Appl. No.: 08/277,556
Filed: Jul. 19, 1994

[30] Foreign Application Priority Data

Jul. 23, 1993 [JP] Japan ..... 5-182583

[51] Int. Cl.[7] ..... G01N 27/26; C12M 1/34

[52] U.S. Cl. ..... 204/403; 204/418; 204/415; 435/287.9; 435/817; 205/777.5; 205/778

[58] Field of Search ..... 204/403, 415, 204/418; 435/817, 287.9; 205/777.5, 778

[56] References Cited

U.S. PATENT DOCUMENTS

| | | | |
|---|---|---|---|
| 5,120,420 | 6/1992 | Nankai et al. | 204/403 |
| 5,192,415 | 3/1993 | Yoshioka et al. | 204/403 |
| 5,229,282 | 7/1993 | Yoshioka et al. | 204/403 |
| 5,512,159 | 4/1996 | Yoshioka et al. | 204/403 |

FOREIGN PATENT DOCUMENTS

| | | |
|---|---|---|
| 0 251 915 | 1/1988 | European Pat. Off. . |
| 0 502 504 | 9/1992 | European Pat. Off. . |
| 3537915 | 4/1987 | Germany . |
| 1-114747 | 5/1989 | Japan . |
| 2-062952 | 3/1990 | Japan . |
| WO 90/05910 | 5/1990 | WIPO . |

*Primary Examiner*—Bruce F. Bell
*Attorney, Agent, or Firm*—Akin, Gump, Strauss, Hauer & Feld, L.L.P.

[57] ABSTRACT

A biosensor for rapid quantification of a specific component contained in various biological samples with high accuracy has an electrically insulating base, an electrode system including a working electrode and a counter electrode formed on one face of the insulating base, and a reaction layer formed on the insulating base in close contact with the electrode system. The reaction layer contains at least a hydrophilic polymer, a buffer and an enzyme which is separated from the buffer.

27 Claims, 4 Drawing Sheets

BIOSENSOR AND METHOD FOR PRODUCING THE SAME

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to a biosensor capable of rapidly quantifying a specific component in a sample solution with high accuracy in a simplified manner, and to a method for producing the same.

2. Description of the Related Art

Various types of biosensor have heretofore been proposed as a system for quantifying the specific component in the sample solution without requiring diluting or stirring of the sample solution.

As an example of such biosensors, a glucose Sensor will be described in the following paragraphs. In general, a system combining glucose oxidase with an enzyme electrode or a hydrogen peroxide electrode is already known as a method of quantifying glucose utilizing the enzyme electrode. The glucose oxidase selectively oxidizes a substrate, i.e., β-D-glucose into D-glucono-δ-lactone by using oxygen as an electron acceptor. During this reaction, oxygen is reduced into hydrogen peroxide. By measuring the amount of the oxygen consumed in this reaction by an oxygen electrode, or by measuring the amount of the hydrogen peroxide produced in this reaction by a hydrogen peroxide electrode which utilizes a platinum electrode or the like, the glucose in the sample solution can be quantified.

By the above-mentioned method, the measurement is however adversely influenced with a concentration of the dissolved oxygen depending on the subject of the measurement. Further, the measurement is made completely impossible under a condition lacking oxygen. A type of the glucose sensor that does not use oxygen as the electron acceptor but uses a metal complex or an organic compound such as potassium ferricyanide, a derivative of ferrocene or a derivative of quinone as the electron acceptor has therefore been developed. With this type of biosensor, by oxidizing a reductant of the electron acceptor produced as the result of the enzyme reaction by the electrode, the concentration of the glucose can be determined based on the current consumed for this oxidation reaction. This manner of measurement is not limited to glucose but has been widely applied for the quantification of substrates other than glucose.

As an example of this type of biosensor, a glucose sensor is known (Japanese Laid-Open Patent Publication No. Hei 1-114,747) which will be described below.

The disclosed biosensor has a configuration comprising an electrical insulating base provided with an electrode system including a working electrode and a counter electrode, a filter layer composed of polycarbonate porous film, an electron acceptor carrying layer, an enzyme carrying layer, a buffer carrying layer, and a developing layer composed of woven cellulose, which are sequentially laminated on the insulating base by placing some space from the electrode system. In this configuration, the above-mentioned carrying layers are prepared by impregnating cellulosic porous films with aqueous solutions of the electron acceptor, the enzyme, and the buffer, and then drying the impregnated bodies.

The operation of this glucose sensor is as follows.

The sample solution titrated on the developing layer is first passed to the buffer carrying layer, whereby the pH value of the sample solution is adjusted to a pH value that can give the highest activity to the enzyme by the buffering action of the buffer. Next, the glucose in the sample solution reacts specifically with the glucose oxidase in the enzyme carrying layer. At the same time, the electron acceptor, such as potassium ferricyanide in the electron acceptor carrying layer, is reduced by the electron produced by the above-mentioned reaction to produce potassium ferrocyanide. The amount of the produced potassium ferrocyanide is directly proportional to the concentration of glucose contained in the sample solution. After the substances having a large molecular weight such as protein which disturb the electrode reaction contained in the sample solution are filtered off by the filter layer, the sample solution reaches the electrode system provided on the insulating base. In order to prevent erroneous measurement, part of the electrode system is covered with the insulating layer. By measuring the value of the current for oxidizing the potassium ferrocyanide produced in the sample solution by the electrode system it is possible to determine the glucose concentration of the sample solution.

the configuration of such prior art sensors, however, there is an inconvenience that an adverse influence is given to the responsive current, because wetting of the surface of the insulating base including the electrode system with the sample solution is not necessarily uniform and thus bubbles are retained between the porous body of the filter layer and the insulating base. Further, if the sample solution contains substances liable to be absorbed in the electrode or substances having an electrode activity, there would be a case wherein the response of the sensor is adversely influenced.

As a method for overcoming the above-mentioned inconveniences, the following biosensor is proposed and disclosed in Japanese Laid-Open Patent Publication No. Hei 2-062,952.

In the disclosed configuration, the sensor comprises an electrically insulating base, an electrode system composed of a working electrode, a counter electrode and a reference electrode formed on the insulating base by means of screen printing or the like, and a reaction layer including a hydrophilic polymer, an oxido-reductase, an electron acceptor, and a buffer as well if required, formed on the electrode system in a manner that the reaction layer is in close contact with the electrode system.

When the sample solution containing the substrate is titrated on the reaction layer, the reaction layer dissolves in the sample solution which is thereby adjusted to a pH value at which the highest enzyme activity is achieved by the buffering action of the buffer, the enzyme reacts with the substrate, and the electron acceptor is reduced. After the completion of the enzyme reaction, the reduced electron acceptor is electrochemically oxidized, and the concentration of the substrate contained in the sample solution is derived from the value Of the current consumed for oxidizing the electron acceptor.

In the above-mentioned configuration of the prior art sensor, if the biosensor is moistened, the buffer would be partly mixed with the enzyme to induce a chemical interaction, thereby lowering the enzyme activity and deteriorating the storing property of the biosensor.

SUMMARY OF THE INVENTION

It is therefore a primary object of the present invention to provide a biosensor that can be applied to quantification of a specific component contained in various biological samples in a rapid and simple manner with high accuracy.

It is another object of the present invention to provide a biosensor that can be stored for a long period of time, and can be utilized in quality control of foodstuffs as well as in clinical tests.

It is still another object of the present invention to provide a method for producing such biosensors while avoiding a possible mixing of an enzyme with a buffer during its manufacturing process.

The present invention provides a biosensor comprising, an electrical insulating base, an electrode system including at least a working electrode and a counter electrode which are provided on a face of the insulating base, and a reaction layer formed on the insulating base in close contact with the electrode system; wherein the reaction layer contains at least a hydrophilic polymer, an enzyme and a buffer, and the enzyme being separated from the buffer.

In a preferred embodiment of the present invention, the reaction layer preferably comprises at least two layers, wherein a first layer is in contact with the electrode system and contains the enzyme and the hydrophilic polymer, and a second layer contains the buffer. It is also preferable for the second layer to comprise a lipid of amphipathic (lipophilic and hydrophilic) property.

In another preferred embodiment of the present invention, the reaction layer preferably comprises at least two layers, wherein a first layer is in contact with the electrode system and contains the buffer and the hydrophilic polymer, and a second layer contains the enzyme. It is also preferable for the second layer to comprise a hydrophilic polymer being soluble in an organic solvent that does not dissolve the hydrophilic polymer contained in the first layer.

It is preferable for the reaction layer of the biosensor in accordance with the present invention to contain an electron acceptor.

The present invention also provides a biosensor, wherein the reaction layer preferably comprises at least three layers, and a first layer contains the buffer and the hydrophilic polymer, and a second layer contains the enzyme and the hydrophilic polymer. It is also preferable for the second layer to further comprise an electron acceptor.

Another preferred embodiment of the present invention further comprises a layer containing a lipid, especially an amphipathic lipid, placed to the outermost part of the reaction layer.

In a further preferred embodiment of the present invention, the biosensor comprises a layer consisting essentially of a hydrophilic polymer placed in close contact with the electrode system.

In still another preferred embodiment of the present invention, the layer containing the buffer and the hydrophilic polymer is in close contact with a layer containing the enzyme and the hydrophilic polymer, wherein the hydrophilic polymers are different from each other, and wherein the hydrophilic polymer contained in the upper layer is soluble in an organic solvent that does not dissolve the hydrophilic polymer contained in the underlying layer.

The present invention also provides a method for producing a biosensor which comprises the steps of:

forming a first layer containing an enzyme and a hydrophilic polymer by using water as the medium on a face of an insulating base in close contact with an electrode system including at least a working electrode and a counter electrode which are provided on the insulating base; and forming a second layer containing a buffer on the first layer by using an organic solvent as the medium that does not dissolve the hydrophilic polymer.

In a preferred embodiment of the above-mentioned method, the step of forming the first layer comprises spreading an aqueous solution which dissolves the enzyme and the hydrophilic polymer on the insulating base and drying the spread solution, wherein the step of forming the second layer comprises spreading a solution obtained by dispersing the buffer in an organic solvent solution of a lipid and drying the spread solution.

In another preferred embodiment of the present invention, the step of forming the first layer comprises spreading an aqueous solution which dissolves the enzyme and the hydrophilic polymer on the insulating base and drying the spread solution, wherein the step of forming the second layer comprises spreading a solution obtained by dispersing the buffer in an organic solvent solution of the hydrophilic polymer on the first layer and drying the spread solution.

The present invention also provides a method for producing a biosensor which comprises the steps of:

forming a first layer containing a buffer and a hydrophilic polymer by using water as the medium on a face of an insulating base in close contact with an electrode system including at least a working electrode and a counter electrode provided on the insulating base; and forming a second layer containing a hydrophilic polymer and an enzyme on the first layer by using an organic solvent as the medium that does not dissolve the hydrophilic polymer contained in the first layer.

In a preferred embodiment of the present invention, the step of forming the first layer comprises spreading an aqueous solution which dissolves the buffer and the hydrophilic polymer on the insulating base and drying the spread solution, wherein the step of forming the second layer comprises spreading an organic solvent solution of the hydrophilic polymer on the first layer and drying the spread solution, and further dropping an aqueous solution of the enzyme on the second layer and drying the dropped solution.

It is preferable that the above-mentioned aqueous solution which dissolves the enzyme and the hydrophilic polymer further dissolves an electron acceptor.

In the same manner, it is also preferable that the above-mentioned aqueous solution of the enzyme further dissolves an electron acceptor.

Further, it is preferable that the method further comprises a step of forming a third layer by spreading an organic solvent solution of a lipid over the second layer and drying the spread solution.

While novel features of the invention are set forth in the preceding, the invention, both as to organization and content, can be further understood and appreciated, along with other objects and features thereof, from the following detailed description and example when taken in conjunction with the attached drawings.

DETAILED DESCRIPTION OF THE PREFERRED EMBODIMENTS

Figure 1:
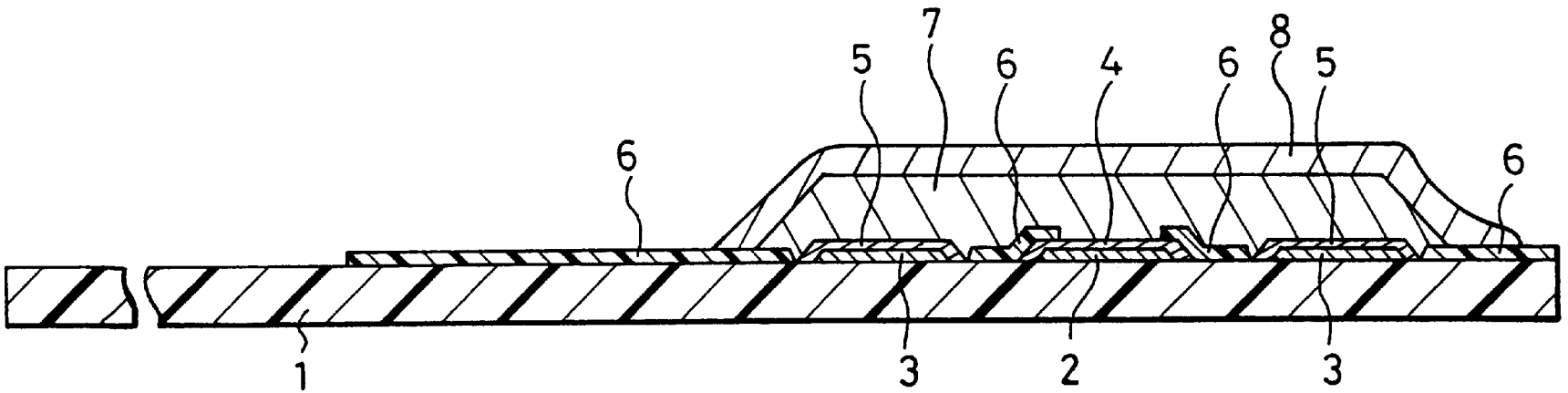
FIG. 1 is a cross-sectional side view showing an essential part of a biosensor prepared in accordance with Example 1 of the present invention.

In the following paragraphs, embodiments of the biosensor and method for producing the same in accordance with the present invention will be described in detail with reference to the attached drawings.

As described in the above, the biosensor of the present invention has a configuration that the reaction layer formed on the electrode system on the insulating base is in close contact with the electrode system, and contains at least the hydrophilic polymer, the enzyme and the buffer, wherein the enzyme is separated from the buffer. Since the reaction layer contains the buffer, even in the case wherein the pH value of the sample solution does not coincide with the pH value which gives the highest enzyme activity, the pH value of the sample solution is automatically adjusted to the pH value which gives the highest activity to the enzyme when the sample solution reaches the buffer contained in the reaction layer. Therefore, there is no need for previously adjusting the pH value of the sample solution with a buffer or the like and it is possible to measure the concentration of the specific component in the sample solution by a simple operation.

Further, by separating the enzyme from the buffer in the reaction layer, it is possible to prevent a partial mixing of the buffer with the enzyme attributable to a possible wetting or moistening of the biosensor and a lowering of the activity of the enzyme attributable to the chemical interaction induced by the mixing, and thus to maintain the enzyme at a condition that stabilizes the enzyme during the storing period of the biosensor.

In the biosensor prepared in accordance with the present invention, the layer containing the buffer is in close contact with the layer containing the enzyme, but the hydrophilic polymers contained in both layers are different from each other. By selecting the hydrophilic polymer contained in the upper layer as the one that is soluble in an organic solvent which does not dissolve the hydrophilic polymer contained in the underlying layer, a direct contact of the buffer with the enzyme can effectively be avoided during the manufacturing process of the biosensor.

The biosensor having the above-mentioned configuration can be obtained by the following manufacturing processes.

One of the processes comprises the steps of forming a first layer composed of the enzyme and the hydrophilic polymer on the insulating base, which is in close contact with the electrode system, by using water as a medium, and forming a second layer containing the buffer on the first layer by using an organic solvent as the medium that does not dissolve the hydrophilic polymer contained in the first layer.

The other process comprises steps of forming a first layer composed of the buffer and the hydrophilic polymer on the insulating base, being in close contact with the electrode system, by using water as a medium, and forming a second layer composed of the enzyme and the hydrophilic polymer on the first layer by using an organic solvent as the medium that does not dissolve the first mentioned hydrophilic polymer.

It is preferable that the biosensor of the present invention has a layer containing a lipid that facilitates an infusion of the sample solution into the reaction layer. In addition to lecithin (phosphatidyl cholin) used in the following examples, an amphipathic (lipophilic and hydrophilic) lipid such as phospholipids, exemplified as phosphatidyl serine, phosphatidyl ethanolamine and the like, are preferable as the lipid.

As the hydrophilic polymer for forming the reaction layer, in addition to carboxymethyl cellulose and polyvinyl pyrrolidone which are used in the following examples, there are exemplified polyvinyl alcohol, water soluble cellulose derivatives such as ethyl cellulose and hydroxypropyl cellulose; gelatin, polyacrylic acid and its salts, starch and its derivatives, maleic anhydride and its salts, polyacrylamide, methacrylate resin, poly-2-hydroxyethyl methacrylate.

Although the description on the following examples is limited to the two-electrode system composed only of the working electrode and the counter electrode, a more accurate measurement can be performed by employing a three-electrode system also including a reference electrode.

In addition to potassium ferricyanide used in the following examples, p-benzoquinone, phenadine methosulfate and ferrocene can be used as the electron acceptor.

As the buffer, any buffer that can demonstrate a pH value which gives the highest activity to the employed enzyme such as any salts of citric acid can freely be used in addition to the phosphate buffer used in the examples.

The present invention can widely be applied to any reaction system where an enzyme participates, such as alcohol sensor, sucrose sensor, and cholesterol sensor, in addition to the exemplified glucose sensor, lactic acid sensor and glucose sensor. In these cases, alcohol oxidase, lactic acid dehydrogenase, cholesterol oxidase, cholesterol dehydrogenase, xanthine oxidase, and an amino acid oxidase can be used in compliance with the specific substance to be quantified, in addition to the fructose dehydrogenase, lactic acid oxidase and glucose oxidase.

As described in the above, the biosensor of the present invention can be applied to the quantification of the specific component contained in the various biological samples in a rapid and simple manner with a high accuracy. Further, since the biosensor can be stored for a long period of time, its value of utilization is great in quality control of foodstuffs as well as in clinical tests.

EXAMPLE 1

(Fructose Sensor I)

Figure 2:
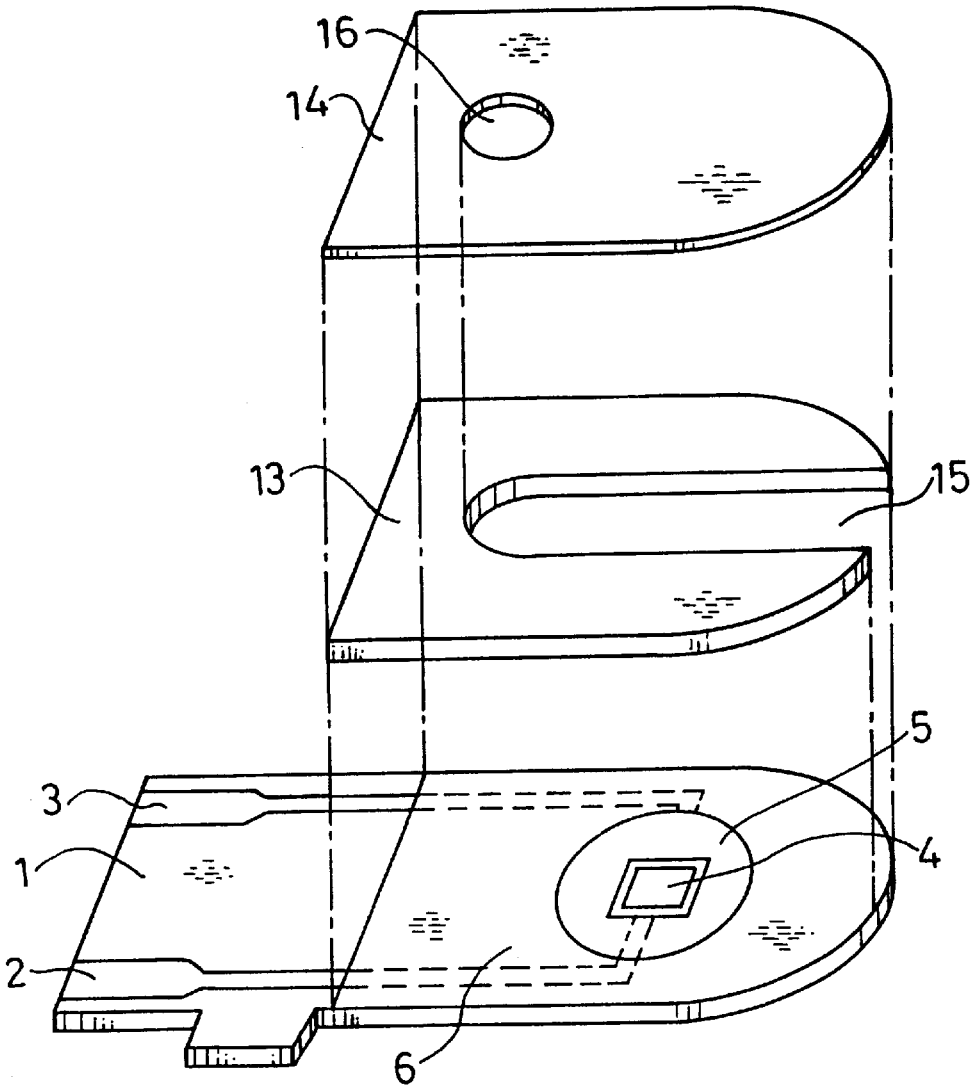
FIG. 2 is an exploded perspective view of the biosensor shown in FIG. 1 removed of its reaction layer.

FIG. 1 is a cross-sectional side view showing a fructose sensor prepared in accordance with an embodiment of the present invention with its cover and a spacer omitted, and FIG. 2 is an exploded perspective view of the fructose sensor with its reaction layer omitted.

An insulating base i is made of polyethylene terephthalate. On the insulating base 1, there are provided lead wires 2 and 3 of silver by means of screen printing. An electrode system including a working electrode 4 and a counter electrode 5 is also formed on the insulating base 1 by printing an electrically-conductive carbon paste containing a resin binder. Further, an insulating layer 6 is formed on the insulating base 1 by printing an insulating paste. The insulating layer 6 maintains areas of the exposed regions of the working electrode 4 and the counter electrode 5 constant, and partly covers the lead wires 2 and 3.

After the electrode region was prepared in this manner, a mixed aqueous solution composed of an aqueous solution (0.5 wt %) of a hydrophilic polymer, sodium salt of carboxymethyl cellulose (hereinafter referred to CMC) which dissolved fructose dehydrogenase (EC1. 1. 99. 11.; hereinafter referred to FDH) as an enzyme and potassium ferricyanide as an electron acceptor, was dropped on the electrode system. By being dried in a hot air dryer at 40° C. for 10 minutes, an FDH-potassium ferricyanide-CMC layer 7 was formed.

On the FDH-potassium ferricyanide-CMC layer 7, there was dropped a dispersion prepared by dispersing microcrystals of potassium dihydrogenphosphate and dipotassium hydrogenphosphate as a buffer in a toluene solution (0.5 wt %) of lecithin as a dispersing medium, which was then dried to form a buffer-lecithin layer 8. Since toluene used as the solvent for forming the layer 8 did not dissolve CMC in the underlying layer, a direct contact of the buffer in the layer 8 with the enzyme in the layer 7 was effectively avoided. Further, by the provision of the layer containing an amphipathic lipid such as lecithin on the surface of the reaction layer, an infusion of the sample solution from the surface into the reaction layer can be made with ease. As described in the above, the reaction layer of the fructose sensor was formed.

The manufacturing process of the biosensor can be simplified by dropping the mixed solutions containing the hydrophilic polymer, the enzyme and the electron acceptor, each in a stroke, and by the subsequent drying. The temperature range during the drying step is preferably from 20° C. to 80° C. which does not lead to a deactivation of the enzyme but is sufficient for completing the drying in a short period of time.

After forming the reaction layer in the above-mentioned manner, the fructose sensor was completed by adhering a cover 14 and a spacer 13 to the insulating base in a positional relationship shown by single dot-dash-lines in FIG. 2. By a simple operation of bringing the sample solution to a contact with a sample supplying inlet 15 provided on a tip of the sensor, the sample solution can easily be introduced into the reaction layer region. Since the supplying amount of the sample solution is dependent on the volume of a space formed by the cover 14 and the spacer 13, there is no need of measuring the supplying amount beforehand.

Further, evaporation of the sample solution can be minimized during the measurement thereby enabling a measurement of high accuracy. In FIG. 2, a reference numeral 16 designates an air inlet opening provided on the cover 14. When a transparent resin is used as the material for constituting the cover 14 and the spacer 13, it is possible to easily observe the condition of the reaction layer and the state of introducing the sample solution from the outside.

Two minutes after supplying 3 $\mu$l of a fructose standard solution as the sample solution to the fructose sensor thus prepared through the sample supplying inlet 15, a pulse voltage of +0.5 V on the basis of the voltage at the counter electrode was applied to the working electrode. Then the anodic current value 5 seconds after the application was measured.

When the sample solution reached the reaction layer, the sample solution dissolved the buffer-lecithin layer 8 to have a desirable pH value, and subsequently dissolved the FDH-potassium ferricyanide-CMC layer 7. During this process, the fructose contained in the sample solution was oxidized so by the FDH, and then the potassium ferricyanide was reduced to a potassium ferrocyanide by shifting of electrons by the oxidation. Next, by the application of the above-mentioned pulse voltage, a current was generated for oxidizing the produced potassium ferrocyanide, and this current value corresponded to the concentration of fructose contained in the sample solution.

The activity of the enzyme employed in the fructose sensor demonstrates its maximum value at pH 4.5 at 37° C. Since the fructose standard solution is substantially neutral, when the standard solution reaches the buffer-lecithin layer 8, its pH value is adjusted to 4.5, thereby making the enzyme activity highest. Further, by separating the buffer from the enzyme, it is possible to improve the storing property of the sensor.

The response obtained with the thus prepared fructose sensor to the fructose standard solution demonstrates a linear relationship for the fructose concentration, and the linear relationship can be maintained in storage for a long period of time.

In the above-mentioned example, in place of the buffer-lecithin layer 8, another buffer-hydrophilic polymer layer may be formed by spreading a solution prepared by dispersing the buffer in a solution of a hydrophilic polymer dissolved in an organic solvent which does not dissolve the CMC contained in the underlying layer, such as an ethanol solution of polyvinyl pyrrolidone, followed by drying.

EXAMPLE 2

(Fructose Sensor II)

Figure 3:
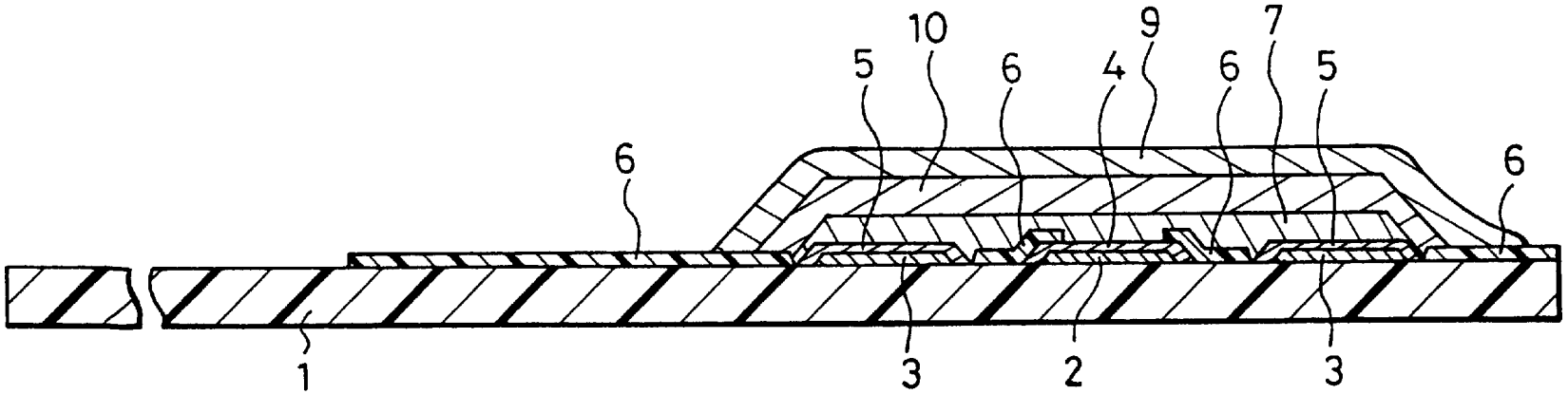
FIG. 3 is a cross-sectional side view showing an essential part of a biosensor prepared in accordance with Example 2 of the present invention.

In a manner similar to that in Example 1, an electrode system composed of the working electrode 4 and the counter electrode 5 was formed on the insulating base 1 made of polyethylene terephthalate by means of screen printing, as shown by FIG. 3. By dropping an aqueous solution (0.5 wt %) of CMC on the electrode system and then drying, a CMC layer was formed. Next, an aqueous solution of the enzyme FDH and the electron acceptor potassium ferricyanide was spread over the CMC layer and then dried to form an FDH-potassium ferricyanide-CMC layer 7. In this case however, the CMC, the FDH as well as the potassium ferricyanide were partially mixed together and formed in a thin film of a thickness of several microns. That is, when the above-mentioned aqueous solution was dropped on the CMC layer, the previously formed CMC layer was once dissolved and then formed a layer 7 in a state partly mixed with the enzyme and the like during the subsequent drying process.

In this case however, since no stirring or the like operation was performed, a completely mixed state was not brought about but a state wherein the surface of the electrode system was covered only with the CMC was brought about by this process. Since the enzyme, the electron acceptor and the like are prevented from a direct contact with the surface of the electrode system in this manner, it is considered that (i) there is a low possibility of an absorption of protein on the surface of the electrode system and a change in the characteristics of the electrode system by a chemical action of a substance having an oxidizing ability such as potassium ferricyanide, and (ii) as a result, it is possible to obtain a sensor having a sensor response with high accuracy.

On this FDH-potassium ferricyanide-CMC layer 7, a dispersion prepared by dispersing microcrystals of potassium dihydrogenphosphate and dipotassium hydrogenphosphate, as the buffer, in an ethanol solution of polyvinyl pyrrolidone (hereinafter referred to PVP) as the hydrophilic polymer in 0.5 wt % was dropped to cover the layer 7 completely, and then dried to form a buffer-PVP layer 10. Since the ethanol employed in forming the layer 10 does not dissolve the CMC contained in the underlying layer, a direct contact of the enzyme in the layer 7 with the buffer contained in the layer 10 can effectively be avoided.

By dropping a toluene solution of lecithin in 0.5 wt % on the buffer-PVP layer 10 and then drying the dropped solution, a lecithin layer 9 was formed on the layer 10. In the above-mentioned manner, a reaction layer of the fructose sensor shown in FIG. 3 was formed.

By combining the insulating base formed with the reaction layer with a spacer 13 and a cover 14 shown by FIG. 2 in a similar manner to that in Example 1, the fructose sensor of this example was completed.

By the provision of the buffer-PVP layer 10, even in a case of selecting a fruit Juice and the like containing solid components such as fruit flesh or pulp as the sample solution, a possible absorption of the above-mentioned flesh or pulp on the surface of the electrode system and its adverse influence on the response of the sensor can effectively be prevented by this buffer-PVP layer, and at the same time, the pH value of the sample solution can be made to a pH value that gives the maximum activity to the enzyme.

The fructose sensor thus prepared demonstrates a rapid and a highly accurate response and has an excellent storing property because the buffer is separated from the enzyme as in Example 1.

EXAMPLE 3

(Lactic Acid Sensor)

Figure 4:
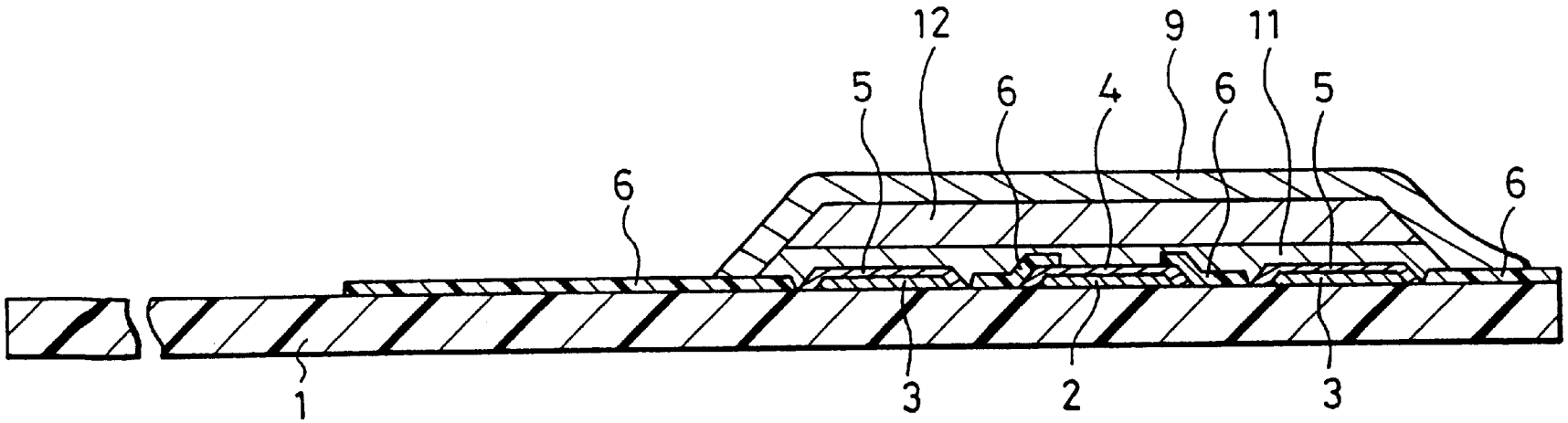
FIG. 4 is a cross-sectional side view showing an essential part of a biosensor prepared in accordance with Example 3 of the present invention.

In a manner similar to that in Example 1, an electrode system was formed on the insulating base 1 made of polyethylene terephthalate by means of screen printing, as shown by FIG. 4. By dropping an aqueous solution (0.5 wt %) of CMC, which also dissolved the buffer, potassium dihydrogenphosphate and dipotassium hydrogenphosphate, on the electrode system and then drying, a buffer-CMC layer 11 was formed. Next, an ethanol solution (0.5 wt %) of PVP was spread over the buffer-CMC layer 11 so that it covered the layer, and then dried to form a PVP layer. An aqueous solution of lactic acid oxidase (available from TOYOBO Co., Ltd., hereinafter referred to LOD) as an enzyme and potassium ferricyanide as an electron acceptor was spread over the PVP layer and then dried. In this case, however, since the PVP layer was partly dissolved in the above-mentioned aqueous solution, an LOD-potassium ferricyanide-PVP layer 12 was formed. Further, since the ethanol employed for forming the PVP layer did not dissolve the CMC contained in the underlying layer, the PVP layer was not mixed with the buffer, and the buffer was completely separated from the enzyme.

By dropping a toluene solution of lecithin in 0.5 wt % on the LOD-potassium ferricyanide-PVP layer 12 and by subsequent drying, a lecithin layer 9 was formed. In the above-mentioned manner, a reaction layer of a lactic acid sensor was formed. FIG. 4 is a configuration of the reaction layer of the lactic acid sensor.

After forming the reaction layer in the above-mentioned manner, the lactic acid sensor of this example was completed by combining the insulating base formed with the reaction layer with a spacer 13 and a cover 14 shown by FIG. 2 in a unitary body in a manner similar to that in Example 1.

Three (3) $\mu$l of a sample solution prepared by diluting lactic acid with pure water to have a predetermined concentration was supplied to the lactic acid sensor thus prepared through a sample supplying inlet 15 thereof. The sample solution rapidly reached a region of air outlet 16 to dissolve the reaction layer on the electrode system.

When supplied with a sample solution, the reaction layer was immediately dissolved in the sample solution, and the buffer contained in the buffer-CMC layer 11 was dissolved in the sample solution to give a desired pH value to the sample solution.

One minute after the supply of the sample solution, a pulse voltage of +0.5 V on the basis of the voltage at the counter electrode 5 was applied to the working electrode 4 and the anodic current value 5 seconds after the application was measured. As a result of the measurement, a response current value proportional to the concentration of lactic acid in the sample solution was obtained.

Since the optimum pH of the enzyme employed in the lactic acid sensor is in a range from 6 to 7 but the standard solution of lactic acid is more acidic than the value in the range, it is possible to derive the maximum activity of the enzyme by causing the sample solution to reach the buffer-CMC layer and thus adjusting pH value of the sample solution from 6 to 7. Further, since the buffer is separated from the enzyme, the lacti acid sensor has an excellent storing property.

EXAMPLE 4

(Glucose Sensor I)

In a manner similar to that in Example 1, an electrode system identical with the electrode region shown in FIG. 1 was formed on the insulating base 1 made of polyethylene terephthalate by means of screen printing. By dropping an aqueous solution (0.5 wt %) of CMC, which also dissolved the buffer, potassium dihydrogenphosphate and dipotassium hydrogenphosphate, on the electrode system and then drying, a buffer-CMC layer was formed. Next, an ethanol solution prepared by dispersing lipid-modified glucose oxidase (hereinafter referred to as lipid-modified GOD) as an enzyme and potassium ferricyanide as an electron acceptor was spread over the buffer-CMC layer to cover the layer and then dried to form a lipid-modified GOD-potassium ferricyanide layer. After a reaction layer was formed in the above-mentioned manner, it was combined with a spacer 13 and a cover 14 shown by FIG. 2 in a unitary body, whereby the glucose sensor of this example was completed.

The above-mentioned lipid-modified GOD can be obtained by adding glucose oxidase (available from TOYOBO Co., Ltd.) to a solution prepared by dispersing an amphipathic lipid, DC-3-12L in water, standing still at 4° C. for 1.5 days, and freeze-drying the stood product. The lipid-modified GOD is easily dispersible in an organic solvent without being agglomerated, and is also soluble in water.

EXAMPLE 5

(Glucose Sensor II)

In a manner similar to that in Example 1, an electrode system identical with the electrode system shown in FIG. 1 was formed on the insulating base 1 made of polyethylene terephthalate by means of screen printing.

After producing the electrode system in the above-mentioned manner, a buffer-potassium ferricyanide-CMC layer was formed by dropping an aqueous solution of CMC in 0.5 wt %, which also dissolved potassium dihydrogenphosphate and dipotassium hydrogenphosphate as a buffer, and potassium ferricyanide as an electron acceptor, on the electrode system, followed by drying. Next, a benzene solution of lipid-modified GOD as the enzyme was spread over to cover the buffer-potassium ferricyanide-CMC layer, and then dried to form a lipid-modified GOD layer. After forming a reaction layer on the insulating base in the above-mentioned manner, the insulating base was combined with a spacer 13 and a cover 14 shown by FIG. 2 in a unitary body in a manner similar to that in Example 1, whereby the glucose sensor of this example was completed.

In the foregoing embodiments, although the electrode system was formed by means of screen printing with an electrically-conductive paint, it may alternately be formed by sputtering of platinum. In this case, the potassium ferricyanide employed as the electron acceptor can be dispensed with; in this enzyme reaction, hydrogen peroxide generated by reducing the oxygen in the substrate solution in proportion to the concentration of lactic acid (or glucose) can be detected by the platinum electrodes, thereby quantifying the concentration of the lactic acid (or glucose).

It is understood that various other modifications will be apparent to and can be readily made by those skilled in the art to which this invention pertains without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof, by those skilled in the art to which this invention pertains.

What is claimed is:

1. A method for producing a biosensor comprising the steps of:

forming a first layer containing an enzyme and a hydrophilic polymer by using water as the medium on a face of an insulating base in close contact with an electrode system including a working electrode and a counter electrode which are provided on said insulating base; and forming a second layer containing a buffer on said first layer by using an organic solvent solution of a lipid which does not dissolve said hydrophilic polymer.

2. The method for producing a biosensor in accordance with claim 1, wherein said step of forming the first layer comprises spreading an aqueous solution which dissolves the enzyme and the hydrophilic polymer on the insulating base and drying the spread solution, and wherein said step of forming the second layer comprises spreading a solution obtained by dispersing the buffer in an organic solvent solution and drying the spread solution.

3. The method for producing a biosensor in accordance with claim 2, wherein said aqueous solution which dissolves the enzyme and the hydrophilic polymer further dissolves an electron acceptor.

4. A method for producing a biosensor comprising the steps of:

forming a first layer containing a buffer and a hydrophilic polymer by using water as the medium on a face of an insulating base in close contact with an electrode system including a working electrode and a counter electrode provided on said insulating base; and forming a second layer containing a hydrophilic polymer and an enzyme on said first layer by using an organic solvent as the medium that does not dissolve said hydrophilic polymer contained in the first layer.

5. The method for producing a biosensor in accordance with claim 4, wherein said step of forming the first layer comprises spreading an aqueous solution which dissolves the buffer and the hydrophilic polymer on the insulating base and drying the spread solution, and wherein said step of forming the second layer comprises spreading an organic solvent solution of the hydrophilic polymer on the first layer and drying the spread solution, and further dropping an aqueous solution of the enzyme on the second layer and drying the dropped solution.

6. The method for producing a biosensor in accordance with claim 5, wherein said aqueous solution of the enzyme further dissolves an electron acceptor.

7. The method for producing a biosensor in accordance with claim 5, further comprising a step of forming a third layer by spreading an organic solvent solution of a lipid over the second layer and drying the spread solution.

8. A method for producing a biosensor comprising:

a first step of spreading an aqueous solution containing a hydrophilic polymer and a buffer on an insulating base in close contact with an electrode system including a working electrode and a counter electrode provided on a face of said insulating base and drying the spread solution, and a second step of spreading an organic solvent solution containing at least an enzyme and a hydrophilic polymer over the layer and drying the spread solution.

9. The method for producing a biosensor in accordance with claim 8, wherein either of said aqueous solution employed in said first step on the organic solvent solution employed in said second step further contains an electron acceptor.

10. The method for producing a biosensor in accordance with claim 9, wherein the organic solvent solution employed in said second step further contains a hydrophilic polymer.

11. A method for producing a biosensor comprising the steps of:

forming a first layer containing an enzyme and a hydrophilic polymer by using water as the medium on a face of an insulating base in close contact with an electrode system including a working electrode and a counter electrode which are provided on said insulating base; and forming a second layer containing a buffer on said first layer by using an organic solvent solution of a hydrophilic polymer, which solvent does not dissolve said hydrophilic polymer contained in the first layer.

12. The method for producing a biosensor in accordance with claim 11, further comprising a step of forming a third layer by spreading an organic solvent solution of a lipid over the second layer and drying the spread solution.

13. The method for producing a biosensor in accordance with claim 11, wherein said step of forming the first layer comprises spreading an aqueous solution which dissolves the enzyme and the hydrophilic polymer on the insulating base and drying the spread solution, and wherein said step of forming the second layer comprises spreading a solution obtained by dispersing the buffer in the organic solvent solution and drying the spread solution.

14. The method for producing a biosensor in accordance with claim 13, wherein said aqueous solution which dissolves the enzyme and the hydrophilic polymer further dissolves an electron acceptor.

[15. The method for producing a biosensor in accordance with claim 13, wherein said aqueous solution which dissolves the enzyme and the hydrophilic polymer further dissolves an electron acceptor.]

16. A biosensor comprising:

an electrical insulating base, an electrode system including a working electrode and a counter electrode which are provided on a face of said insulating base, and a reaction layer formed on said insulating base in close contact with said electrode system; wherein said reaction layer is a laminate of at least two layers, and wherein a first reaction layer is in contact with said electrode system and contains an enzyme, an electron acceptor and a hydrophilic polymer, and a second reaction layer is on top of said first reaction layer and contains a buffer and a lipid, said enzyme being separated from said buffer.

17. A biosensor comprising, an electrical insulating base, an electrode system including a working electrode and a counter electrode which are provided on a face of said insulating base, and a reaction layer formed on said insulating base in close contact with said electrode system; wherein said reaction layer is a laminate of at least two layers, and wherein a first reaction layer is in contact with said electrode system and contains an enzyme and an electron acceptor and a second reaction layer is on top of said first reaction layer and contains a buffer and a hydrophilic polymer, said enzyme being separated from said buffer.

18. A biosensor comprising, an electrical insulating base, an electrode system including a working electrode and a counter electrode which are provided on a face of said insulating base and a reaction layer formed on said insulating base in close contact with said electrode system; wherein said reaction layer is a laminate of at least three layers, and wherein a first reaction layer is in contact with said electrode system and contains an enzyme and an electron acceptor, a second reaction layer is on top of said first reaction layer and contains a buffer and a hydrophilic polymer and a third reaction layer is on top of said second reaction layer and contains a lipid, said enzyme being separated from said buffer.

*19. A method for producing a biosensor comprising the steps of:*

*forming a first layer containing a buffer and a hydrophilic polymer by using water as the medium on a face of an insulating base in close contact with an electrode system including a working electrode and counter electrode provided on said insulating base; and forming a second layer containing a lipid-modified enzyme on said first layer by using an organic solvent as the medium that does not dissolve said hydrophilic polymer contained in the first layer.*

*20. The method for producing a biosensor in accordance with claim 19, wherein said step of forming the first layer comprises spreading an aqueous solution which dissolves the buffer and the hydrophilic polymer on the insulating base and drying the spread solution, and wherein said step of forming the second layer comprises spreading an organic solvent solution of the lipid-modified enzyme on the first layer and drying the spread solution.*

*21. The method for producing a biosensor in accordance with claim 20, wherein said aqueous solution further dissolves an electron acceptor.*

*22. The method for producing a biosensor in accordance with claim 20, wherein said organic solvent solution of the lipid-modified enzyme is dispersed with an electron acceptor.*

*23. The method for producing a biosensor in accordance with claim 19, wherein said step of forming the first layer comprises spreading an aqueous solution which dissolves the buffer and the hydrophilic polymer on the insulating base and drying the spread solution, and wherein said step of forming the second layer comprises spreading an organic solvent dispersed with the lipid-modified enzyme on the first layer and drying the spread solution.*

*24. The method for producing a biosensor in accordance with claim 23, wherein said aqueous solution further dissolves an electron acceptor.*

*25. The method for producing a biosensor in accordance with claim 23, wherein said organic solvent solution is further dispersed with an electron acceptor.*

*26. A biosensor comprising:*

*an electrical insulating base,*

*an electrode system including a working electrode and a counter electrode which are provided on a face of said insulating base, and*

*a reaction layer formed on said insulating base in close contact with said electrode system;*

*wherein said reaction layer is a laminate of at least two layers, and*

*wherein a first layer is in contact with said electrode system and contains a buffer and a hydrophilic polymer, and a second layer is on top of said first layer and contains a lipid-modified enzyme, said enzyme being separated from said buffer.*

*27. The biosensor in accordance with claim 26, wherein said first layer contains an electron acceptor.*

*28. The biosensor in accordance with claim 26, wherein said second layer contains an electron acceptor.*

* * * * *